US010160696B2

(12) United States Patent
Jaber et al.

(10) Patent No.: US 10,160,696 B2
(45) Date of Patent: Dec. 25, 2018

(54) HEAT MANAGEMENT IN ETHYLENE OLIGOMERIZATION

(71) Applicant: NOVA Chemicals (International) S.A., Fribourg (CH)

(72) Inventors: Isam Jaber, Calgary (CA); Ian Ronald Jobe, Calgary (CA); P Scott Chisholm, Calgary (CA); Andrzej Krzywicki, Calgary (CA); Charles Ashton Garret Carter, Calgary (CA); Vernon Lindsay Strom, Calgary (CA); Kamal Elias Serhal, Calgary (CA); Eric Clavelle, Calgary (CA); Stephen John Brown, Calgary (CA); Yves Lacombe, Calgary (CA); Anita Sylvia Magis, Calgary (CA); Mackenzie Alexander Harris, Calgary (CA); Russell Kirk Archer, Calgary (CA); Keith WAyne Besenski, Calgary (CA); Michel Berghmans, Calgary (CA); Oleksiy Golovchenko, Airdrie (CA); Dale Alexander Sieben, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 15/136,015

(22) Filed: Apr. 22, 2016

(65) Prior Publication Data
US 2016/0237000 A1 Aug. 18, 2016

Related U.S. Application Data

(63) Continuation of application No. 13/293,889, filed on Nov. 10, 2011.

(30) Foreign Application Priority Data

Dec. 1, 2010 (CA) ..................... 2723515

(51) Int. Cl.
C07C 2/04 (2006.01)
C07C 2/36 (2006.01)

(52) U.S. Cl.
CPC ............ *C07C 2/36* (2013.01); *C07C 2523/26* (2013.01); *C07C 2531/14* (2013.01); *C07C 2531/24* (2013.01); *Y02P 20/52* (2015.11)

(58) Field of Classification Search
CPC ... C07C 2/36; C07C 2531/24; C07C 2531/14; C07C 2/08; C07C 2/26
USPC ....... 585/520, 532, 510, 511, 512, 527, 530, 585/533
See application file for complete search history.

(56) References Cited

U.S. PATENT DOCUMENTS

| 2,474,592 | A | | 6/1949 | Palmer | |
|---|---|---|---|---|---|
| 3,700,710 | A | * | 10/1972 | Mottus | B01J 37/348 556/180 |
| 4,007,016 | A | | 2/1977 | Weber | |
| 4,121,029 | A | | 10/1978 | Irvin et al. | |
| 4,328,973 | A | * | 5/1982 | Delbridge | F16J 15/40 277/304 |
| 5,198,563 | A | | 3/1993 | Reagen et al. | |
| 6,319,996 | B1 | | 11/2001 | Burke et al. | |
| 6,800,702 | B2 | * | 10/2004 | Wass | B01J 31/1616 502/104 |
| 7,414,006 | B2 | * | 8/2008 | McConville | B01J 31/1815 502/103 |
| 7,786,336 | B2 | | 8/2010 | Zhang et al. | |
| 2002/0016521 | A1 | * | 2/2002 | Culver | C07C 2/32 585/527 |
| 2006/0025640 | A1 | * | 2/2006 | Karjala | C08F 210/16 585/17 |
| 2006/0173226 | A1 | * | 8/2006 | Blann | B01J 31/1608 585/511 |
| 2008/0027188 | A1 | * | 1/2008 | Small | B01J 31/143 526/113 |
| 2009/0118117 | A1 | | 5/2009 | Elowe et al. | |

FOREIGN PATENT DOCUMENTS

| CN | 1490291 A | * | 4/2004 |
|---|---|---|---|
| WO | 02/04119 A1 | | 1/2002 |
| WO | 2004/056478 A1 | | 7/2004 |
| WO | 2004/056479 A1 | | 7/2004 |
| WO | 2007/016996 A1 | | 2/2007 |
| WO | 2009/060342 A2 | | 5/2009 |
| WO | 2009/060343 A1 | | 5/2009 |

OTHER PUBLICATIONS

Naqvi, S., "1-Hexene From Ethylene by the Phillips Trimerization Technology," SRI Consulting PEP Review Jan. 8, 1995, http://www.sriconsulting.com/PEP/Reports/Phase_95/RW95-1-8/RW95-1-8.html, Dec. 1997.*
Haynes, W.M. "CRC Handbook of Chemistry and Physics" 95th Edition, Internet version (2005), pp. 298 and 426.*
Carter, Anthea; Cohen, Steven A.; Cooley, Neil A.; Murphy, Aden; Scutt, James and Wass, Duncan F.; High activity ethylene trimerisation catalysts based on diphosphine ligands; Copyright: The Royal Society of Chemistry; 2002; Downloaded: www.rsc.org/chemcomm; pp. 858-859.

* cited by examiner

*Primary Examiner* — In Suk C Bullock
*Assistant Examiner* — Aaron W Pierpont
(74) *Attorney, Agent, or Firm* — Gary F. Matz

(57) ABSTRACT

The oligomerization of ethylene using a chromium catalyst having a heteroatomic ligand may be used to provide oligomerization products that are selective towards hexene and/or octene. However, such processes also typically produce some polymer as an undesirable by product. The present invention is directed towards improvements in the selective oligomerization of ethylene.

14 Claims, No Drawings

HEAT MANAGEMENT IN ETHYLENE OLIGOMERIZATION

CROSS REFERENCE TO RELATED PATENT APPLICATION

This application is a continuation of U.S. application Ser. No. 13/293,889, filed on Nov. 10, 2011, entitled "Heat Management in Ethylene Oligomerization", which claims priority to Canadian Patent Application 2723515, filed on Dec. 1, 2010, which are herein incorporated by reference in their entirety.

FIELD OF THE INVENTION

This invention relates to selective ethylene oligomerization reactions.

BACKGROUND OF THE INVENTION

Alpha olefins are commercially produced by the oligomerization of ethylene in the presence of a simple alkyl aluminum catalyst (in the so called "chain growth" process) or alternatively, in the presence of an organometallic nickel catalyst (in the so called Shell Higher Olefins, or "SHOP" process). Both of these processes typically produce a crude oligomer product having a broad distribution of alpha olefins with an even number of carbon atoms (i.e. butene-1, hexene-1, octene-1 etc.). The various alpha olefins in the crude oligomer product are then typically separated in a series of distillation columns. Butene-1 is generally the least valuable of these olefins as it is also produced in large quantities as a by-product in various cracking and refining processes. Hexene-1 and octene-1 often command comparatively high prices because these olefins are in high demand as comonomers for linear low density polyethylene (LLDPE).

Technology for the selective trimerization of ethylene to hexene-1 has been recently put into commercial use in response to the demand for hexene-1. The patent literature discloses catalysts which comprise a chromium source and a pyrrolide ligand as being useful for this process—see, for example, U.S. Pat. No. 5,198,563 (Reagen et al., assigned to Phillips Petroleum).

Another family of highly active trimerization catalysts is disclosed by Wass et al. In WO 02/04119 (now U.S. Pat. Nos. 7,143,633 and 6,800,702). The catalysts disclosed by Wass et al. are formed from a chromium source and a chelating diphosphine ligand and are described in further detail by Carter et al. (Chem. Comm. 2002, p 858-9). As described in the Chem. Comm. paper, these catalysts preferably comprise a diphosphine ligand in which both phosphine atoms are bonded to two phenyl groups that are each substituted with an ortho-methoxy group. Hexene-1 is produced with high activity and high selectivity by these catalysts.

Similar diphosphine/tetraphenyl ligands are disclosed by Blann et al. in WO04/056478 and WO 04/056479 (now US 2006/0229480 and US 2006/0173226). However, in comparison to the ligands of Wass et al., the disphosphine/tetraphenyl ligands disclosed by Blann et al. generally do not contain polar substituents in ortho positions. The "tetraphenyl" diphosphine ligands claimed in the '480 application must not have ortho substituents (of any kind) on all four of the phenyl groups and the "tetraphenyl" diphosphine ligands claimed in '226 are characterized by having a polar substituent in a meta or para position. Both of these approaches are shown to reduce the amount of hexenes produced and increase the amount of octene (in comparison to the ligands of Wass et al.). Other bridged diphosphine ligands that are useful for the selective oligomerization of ethylene are disclosed in the literature. The formation of polymer as a by-product is a general problem with many of these ligands.

SUMMARY OF THE INVENTION

In one embodiment, the present invention provides a solution process for the oligomerization of ethylene, said process comprising contacting ethylene with:
a) oligomerization catalyst;
b) an activator; and
c) a solvent for said catalyst,
said process being conducted under oligomerization conditions in an oligomerization reactor system characterized in that said process is conducted with process equipment that includes:
1) a first heat exchanger that is used to provide heat to said process; and
2) a second heat exchanger that is used to remove heat from said oligomerization reactor system.

It will be appreciated by those skilled in the art that the present invention is somewhat unusual in that heat is both provided to and removed from the oligomerization process. It is recognized that this process is not optimal from the perspective of energy efficiency. However, the present process provides the capability to improve temperature control, particularly during non-steady state operations such as encountered when fluctuations in process flows or poison levels (especially during start up) cause the reactor to become unstable.

We have observed severe reactor fouling when the temperature in the oligomerization reactor suddenly drops and the process of this invention mitigates this problem. This invention is generally useful for any selective oligomerization process. It is especially useful when the catalyst comprises a bridged diphosphine ligand and when the reactor system includes a liquid full CSTR.

For further clarity: the two heat exchangers described above are independent of each other—that is, they both may be operated at the same time. (This is to distinguish the present invention from a common design in which a single heat exchanger may be used either to heat or cool a process stream).

In another embodiment, the ethylene feed stream is equipped with a third heat exchanger to cool the feed stream (as discussed later, with reference to the so called "solution absorber"). In a preferred embodiment, the "first heat exchanger" (i.e. the heat exchanger that may be used to provide heat to the process) is located "downstream" of the third heat exchanger—i.e. the third heat exchanger may be used to heat the feed stream before the feed stream is sent to the reactor. In plain language, the first heat exchanger may be used to heat the cooled feed from the "third" heat exchanger. It will be recognized by those skilled in the art that such a cooling/heating cycle is not energy efficient and that it should be avoided during steady state operations. However, this ability to both cool and heat the feed stream has been found to be useful to mitigate unwanted polymer formation during unsteady operations (such as encountered at start up or during a reactor upset).

DETAILED DESCRIPTION OF THE PREFERRED EMBODIMENTS

Part A Catalyst System

The preferred catalyst system used in the process of the present invention must contain three essential components, namely:

(i) a source of chromium that is soluble in the process solvent;

(ii) a diphosphine ligand; and (iii) an activator.

Preferred forms of each of these components are discussed below.

Chromium Source ("Component (i)")

Any source of chromium that is soluble in the process solvent and which allows the oligomerization process of the present invention to proceed may be used. Preferred chromium sources include chromium trichloride; chromium (III) 2-ethylhexanoate; chromium (III) acetylacetonate and chromium carbonyl complexes such as chromium hexacarbonyl. It is preferred to use very high purity chromium compounds as these should generally be expected to minimize undesirable side reactions. For example, chromium acetylacetonate having a purity of higher than 99% is commercially available (or may be readily produced from 97% purity material—using recrystallization techniques that are well known to those skilled in the art).

Ligand Used in the Oligomerization Process ("Component (ii)")

In general, the ligand used in the oligomerization process of this invention is defined by the formula $(R^1)(R^2)$—$P^1$-bridge-$P^2(R^3)(R^4)$ wherein $R^1$, $R^2$, $R^3$ and $R^4$ are independently selected from the group consisting of hydrocarbyl and heterohydrocarbyl and the bridge is a divalent moiety that is bonded to both phosphorus atoms.

The term hydrocarbyl as used herein is intended to convey its conventional meaning—i.e. a moiety that contains only carbon and hydrogen atoms. The hydrocarbyl moiety may be a straight chain; it may be branched (and it will be recognized by those skilled in the art that branched groups are sometimes referred to as "substituted"); it may be saturated or contain unsaturation and it may be cyclic. Preferred hydrocarbyl groups contain from 1 to 20 carbon atoms. Aromatic groups—especially phenyl groups—are especially preferred. The phenyl may be unsubstituted (i.e. a simple $C_6H_5$ moiety) or contain substituents, particularly at an ortho (or "o") position.

Similarly, the term heterohydrocarbyl as used herein is intended to convey its conventional meaning—more particularly, a moiety that contains carbon, hydrogen and heteroatoms (such as O, N, R and S). The heterohydrocarbyl groups may be straight chain, branched or cyclic structures. They may be saturated or contain unsaturation. Preferred heterohydrocarbyl groups contain a total of from 2 to 20 carbon+heteroatoms (for clarity, a hypothetical group that contains 2 carbon atoms and one nitrogen atom has a total of 3 carbon+heteroatoms).

It is preferred that each of $R^1$, $R^2$, $R^3$ and $R^4$ is a phenyl group (with an optional substituent in an ortho position on one or more of the phenyl groups).

Highly preferred ligands are those in which $R^1$ to $R^4$ are independently selected from the group consisting of phenyl, o-methylphenyl (i.e. ortho-methylphenyl), o-ethylphenyl, o-isopropylphenyl and o-fluorophenyl. It is especially preferred that none of $R^1$ to $R^4$ contains a polar substituent in an ortho position. The resulting ligands are useful for the selective tetramerization of ethylene to octene-1 with some co product hexene also being produced. The term "bridge" as used herein with respect to the ligand refers to a divalent moiety that is bonded to both of the phosphorus atoms in the ligand—in other words, the "bridge" forms a link between $P^1$ and $P^2$. Suitable groups for the bridge include hydrocarbyl and an inorganic moiety selected from the group consisting of $N(CH_3)$—$N(CH_3)$—, —$B(R^6)$—, —$Si(R^6)_2$—, —$P(R^6)$— or —$N(R^6)$— where $R^8$ is selected from the group consisting of hydrogen, hydrocarbyl and halogen.

It is especially preferred that the bridge is —$N(R^5)$— wherein $R^5$ is selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof and an aryl group substituted with any of these substituents. A highly preferred bridge is amino isopropyl (i.e. when $R^5$ is isopropyl).

In one embodiment, two different types of ligands are used to alter the relative amounts of hexene and octene being produced. For clarity: the use of a ligand that produces predominantly hexene may be used in combination with a ligand that produces predominantly octene.

Activator ("Component (iii)")

The activator (component (iii)) may be any compound that generates an active catalyst for ethylene oligomerization with components (i) and (ii). Mixtures of activators may also be used. Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminium compounds include compounds of the formula $AlR_3$, where each R is independently $C_1$-$C_{12}$ alkyl, oxygen or halide, and compounds such as $LiAlH_4$ and the like. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available alumoxanes are generally believed to be mixtures of linear and cyclic compounds. The cyclic alumoxanes can be represented by the formula $[R^6AlO]_s$ and the linear alumoxanes by the formula $R^7(R^8AlO)_s$ wherein s is a number from about 2 to 50, and wherein $R^6$, $R^7$, and $R^8$ represent hydrocarbyl groups, preferably $C_1$ to $C_6$ alkyl groups, for example methyl, ethyl or butyl groups. Alkylalumoxanes especially methylalumoxane (MAO) are preferred.

It will be recognized by those skilled in the art that commercially available alkylalumoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylalumoxane are generally quoted herein on a molar basis of aluminium (and include such "free" trialkylaluminium).

Examples of suitable organoboron compounds are boroxines, $NaBH_4$, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, trityltetra(pentafluorophenyl)borate and tris (pentafluorophenyl) boron.

Activator compound (iii) may also be or contain a compound that acts as a reducing or oxidizing agent, such as sodium or zinc metal and the like, or oxygen and the like.

In the preparation of the catalyst systems used in the present invention, the quantity of activating compound to be employed is easily determined by simple testing, for example, by the preparation of small test samples which can be used to oligimerize small quantities of ethylene and thus to determine the activity of the produced catalyst. It is generally found that the quantity employed is sufficient to provide 0.5 to 1000 moles of aluminium (or boron) per mole of chromium. MAO is the presently preferred activator. Molar Al/Cr ratios of from 1/1 to 500/1 are preferred.

Part B Process Conditions

The chromium (component (i)) and ligand (component (ii)) may be present in any molar ratio which produces oligomer, preferably between 100:1 and 1:100, and most preferably from 10:1 to 1:10, particularly 3:1 to 1:3. Generally the amounts of (i) and (ii) are approximately equal, i.e. a ratio of between 1.5:1 and 1:1.5.

Components (i)-(ii) of the catalyst system utilized in the present invention may be added together simultaneously or sequentially, in any order, and in the presence or absence of ethylene in any suitable solvent, so as to give an active catalyst. For example, components (i), (ii) and (iii) and ethylene may be contacted together simultaneously, or components (i), (ii) and (iii) may be added together simultaneously or sequentially in any order and then contacted with ethylene, or components (i), (ii) and (iii) may be added together to form an isolable metal-ligand complex and then added to component (iii) and contacted with ethylene, or components (i), (ii) and (iii) may be added together to form an isolable metal-ligand complex and then contacted with ethylene. Suitable solvents for contacting the components of the catalyst or catalyst system include, but are not limited to, hydrocarbon solvents such as heptane, toluene, 1-hexene and the like, and polar solvents such as diethyl ether, tetrahydrofuran, acetonitrile, dichloromethane, chloroform, chlorobenzene, acetone and the like. A preferred solvent is the oligomer product that is produced by the present process or some fraction thereof—such as hexene, octene or a mixture of the two.

For further clarity: the catalyst components may be mixed together in the oligomerization reactor, or—alternatively—some or all of the catalyst components may be mixed together outside of the oligomerization reactor. In general, it is preferred to mix the catalyst components outside of the reactor (due to comparative ease of control) then add the catalyst to the reactor shortly thereafter (because "aged" catalyst may suffer from some loss of activity). This method of catalyst synthesis is illustrated in the examples. The solvent that is used to prepare the catalyst is preferably the olefinic product that is produced by the reactor (or some portion thereof). We have found that the use of octene generally works well. However, some catalyst components have comparatively low solubility in octene. For example, MAO that is made solely with trimethylaluminum (as opposed to "modified MAO" which also contains some higher alkyl aluminum, such as triisobutyl aluminum) is less soluble in octene than in some cyclic hydrocarbons such as xylene or tetralin. Accordingly, when one or more catalyst components are mixed together outside of the oligomerization reactor, the use of ortho-xylene or tetralin as the solvent may be preferred. The xylene may be a mixture of ortho, meta and para isomers—i.e. it is not necessary to use a pure isomer.

A variety of methods are known to purify solvents used in the oligomerization process including use of molecular sieves (3A), adsorbent alumina and supported de-oxo copper catalyst. Several configurations for the purifier system are known and depend on the nature of the impurities to be removed, the purification efficiency required and the compatibility of the purifier material and the process solvent. In some configurations, the process solvent is first contacted with molecular sieves, followed by adsorbent alumina, then followed by supported de-oxo copper catalyst and finally followed by molecular sieves. In other configurations, the process solvent is first contacted with molecular sieves, followed by adsorbent alumina and finally followed by molecular sieves. In yet another configuration, the process solvent is contacted with adsorbent alumina. When alpha olefinic solvents are used in the process, the preferred purifier system consists of molecular sieves, followed by adsorbent alumina and finally followed by another set of molecular sieves.

The catalyst components (i), (ii) and (iii) utilized in the present invention can be unsupported or supported on a support material, for example, silica, alumina, $MgCl_2$ or zirconia, or on a polymer, for example polyethylene, polypropylene, polystyrene, or poly(aminostyrene). If desired the catalysts can be formed in situ in the presence of the support material, or the support material can be pre-impregnated or premixed, simultaneously or sequentially, with one or more of the catalyst components. The quantity of support material employed can vary widely, for example from 100,000 to 1 gram per gram of metal present in the transition metal compound. In some cases, the support material can also act as or as a component of the activator compound (iii). Examples include supports containing alumoxane moieties.

Oligomerization reactions can generally be conducted under solution phase, slurry phase, gas phase or bulk phase conditions. Suitable temperatures range from 10° C. to +300° C. preferably from 10° C. to 100° C., especially from 20 to 80° C. Suitable pressures are from atmospheric to 800 atmospheres (gauge) preferably from 5 atmospheres to 100 atmospheres, especially from 10 to 50 atmospheres.

Irrespective of the process conditions employed, the oligomerization is typically carried out under conditions that substantially exclude oxygen, water, and other materials that act as catalyst poisons. In addition, the reactor is preferably purged with a nonreactive gas (such as nitrogen or argon) prior to the introduction of catalyst. A purge with a solution of MAO and/or aluminum alkyl may also be employed to lower the initial level of catalyst poisons. Also, oligomerizations can be carried out in the presence of additives to control selectivity, enhance activity and reduce the amount of polymer formed in oligomerization processes. Potentially suitable additives include, but are not limited to, hydrogen or a halide source (especially the halide sources disclosed in U.S. Pat. No. 7,786,336, Zhang et al.). Other (optional) additives include antistatic agents (such as the polysulfone polymer sold under the trademark Stadis®) and/or fluorocarbons to mitigate reaction fouling; or amines to alter the hexene/octene ratio of the product oligomer (as disclosed in U.S. application 20090118117, Elowe et al.). The use of hydrogen is especially preferred because it has been observed to reduce the amount of polymer that is formed. It is within the scope of this invention that an oligomerization product might also serve as a solvent or diluent. The preferred catalysts of this invention predominantly produce hexene and octene (as shown in the examples) but smaller quantities of butene and $C_{10}+$ olefins are also produced. The crude product stream may be separated into various fractions using, for example, a conventional distillation system. It is within the scope of this invention to recycle the "whole" oligomer product or some fraction(s) thereof to the reaction for use as the oligomerization solvent/diluents. For example, by recycling a butene rich stream it might be possible to lower the refrigeration load in distillation. Alternatively, the $C_{10}$+ fraction might be preferentially recycled to improve the solubility of one or more components of the catalyst system. Mixtures of inert diluents or solvents also could be employed. The preferred diluents or solvents are aliphatic and aromatic hydrocarbons and halogenated hydrocarbons such as, for example, isobutane, pentane, toluene, xylene, ethylbenzene, cumene, mesitylene, heptane, cyclohexane, methylcyclohexane, 1-hexene, 1-octene, chlorobenzene, dichlorobenzene, and the like, and mixtures such as Isopar™.

Techniques for varying the distribution of products from the oligomerization reactions include controlling process conditions (e.g. concentration of components (i)-(iii), reaction temperature, pressure, residence time) and properly selecting the design of the process and are well known to those skilled in the art.

In another embodiment, a catalyst that produces ethylene homopolymer is deliberately added to the reactor in an amount sufficient to convert from 1 to 5 weight % of the ethylene feed to an ethylene homopolymer. This catalyst is preferably supported. The purpose is to facilitate the removal of by-product polyethylene.

The ethylene feedstock for the oligomerization may be substantially pure or may contain other olefinic impurities and/or ethane. One embodiment of the process of the invention comprises the oligomerization of ethylene-containing waste streams from other chemical processes or a crude ethylene/ethane mixture from a cracker as more fully described in co-pending Canadian patent application 2,708,011 (Krzywicki et al.).

The feedstock is preferably treated to remove catalyst poisons (such as oxygen, water and polar species) using techniques that are well known to those skilled in the art. The technology used to treat feedstocks for polymerizations is suitable for use in the present invention and includes the molecular sieves, alumina and de-oxo catalysts described above for analogous treatment of the process solvent.

Reactor Systems

A general review of suitable reactors for selective oligomerization is provided first, followed by a detailed description of preferred reactor designs. There exist a number of options for the oligomerization reactor including batch, semi-batch, and continuous operation. Oligomerization reactions can generally be performed under a range of process conditions that are readily apparent to those skilled in the art: as a homogeneous liquid phase reaction in the presence or absence of an inert hydrocarbon diluent such as toluene or heptanes; as a two-phase liquid/liquid reaction; as a slurry process where the catalyst is in a form that displays little or no solubility; as a bulk process in which essentially neat reactant and/or product olefins serve as the dominant medium; as a gas-phase process in which at least a portion of the reactant or product olefin(s) are transported to or from a supported form of the catalyst via the gaseous state. Evaporative cooling from one or more monomers or inert volatile liquids is but one (prior art) method that can be employed to effect the removal of heat from the reaction. The reactions may be performed in the known types of gas-phase reactors, such as circulating bed, vertically or horizontally stirred-bed, fixed-bed, or fluidized-bed reactors, liquid-phase reactors, such as a plug-flow reactor, or a continuously stirred tank reactor (CSTR), or a loop reactor, or combinations thereof. A wide range of methods for effecting product, reactant, and catalyst separation and/or purification are known to those skilled in the art and may be employed: distillation, filtration, liquid-liquid separation, slurry settling, extraction, etc. One or more of these methods may be performed separately from the oligomerization reaction or it may be advantageous to integrate at least some with the reaction; a non-limiting example of this would be a process employing catalytic (or reactive) distillation. Also advantageous may be a process which includes more than one reactor, a catalyst kill system between reactors or after the final reactor, or an integrated reactor/separator/purifier. While all catalyst components, reactants, inerts, and products could be employed in the present invention on a once-through basis, it is often economically advantageous to recycle one or more of these materials; in the case of the catalyst system, this might require reconstituting one or more of the catalysts components to achieve the active catalyst system.

More specific reactor designs have been described in the patent literature:

a liquid phase reactor with "bubbling" ethylene feed is taught as a means to mitigate PE formation (WO 2009/060342, Kleingeld et al.);

a liquid phase reactor with an inert, condensable liquid is claimed as a means to improve temperature control (WO 2009/060343, Crildenhuys). The condensable liquid boils from the reaction liquid and is condensed overhead; and the use of a liquid/gas phase reactor in which cooling coils are present in the gas phase head space is described in WO 2007/016996, Fritz et al.).

The present invention provides additional reactor designs for selective oligomerizations. The present invention is characterized (in part) by the requirement that a non adiabatic reactor system is used. The term "non adiabatic" means that heat is added to and/or removed from the oligomerization reactor. The term "reactor system" means that one or more reactors are employed (and the term "non adiabatic reactor system" means that at least one of the reactors is equipped with a heat exchanger that allows heat to be added to or removed from it). One embodiment relates to a CSTR with an external heat exchanger. A second embodiment relates to a tubular plug flow equipped with multiple feed ports for ethylene along the length of the reactor. A third embodiment relates to a combination of a CSTR followed by a tubular reactor. A fourth embodiment provides a loop reactor. A fifth embodiment provides a reactor having an internal cooling system (such as a draft tube reactor).

One preferred CSTR for use in the present invention is equipped at least one external heat exchanger—meaning that the heat exchanger surface(s) are not included within the walls of the CSTR. The term "heat exchanger" is meant to include its broad, conventional meaning. Most importantly, the heat exchanger will preferably be designed so as to allow heating of the reactor contents (which may be desirable during start up) and to provide heat removal during the oligomerization. A preferred external heat exchanger for a CSTR comprises a conventional shell and tube exchanger with a "process" side tube system and a shell for the exchange side. In one embodiment the "process side" (i.e. the side of the exchanger that contains the fluid from the oligomerization process) is a tube that exits the reactor and flows through the shell for heat exchange, then reenters the reactor with cooled (or heated) process fluid. For clarity: during an oligomerization reaction a portion of the hot reactor contents or "process fluid" will flow from the reactor to the external heat exchanger, through a tube. The exterior of the tube comes into contact with cold fluid on the shell side of the exchanger, thus cooling the process fluid. The cooled process fluid is then returned to the reactor.

The use of two of more CSTR reactors in series is also contemplated. In particular, the use of a first CSTR having a small volume followed by a larger CSTR might be used to facilitate startup.

In another embodiment, a heat exchanger is located between two CSTRs. In this embodiment, the product from the first oligomerization reactor leaves that reactor through an exit tube. The oligomerization products in this exit tube are then directed through a heat exchanger. After being cooled by the heat exchanger, the oligomerization products are then directed into a second CSTR. Additional ethylene (and, optionally, catalyst) is added to the second CSTR and further oligomerization takes place.

The amount of heat generated by the oligomerization reaction is generally proportional to the amount of ethylene being oligomerized. Thus, at high rates of oligomerization, a high rate of coolant flow is required in the shell side of the exchanger.

The rate of oligomerization is generally proportional to the amount of ethylene and catalyst that are fed to the CSTR. In one preferred embodiment the ethylene is first contacted with solvent in a mixing vessel that is external to the CSTR. For convenience, this mixing vessel is referred to herein as a "solution absorber". The solution absorber is preferably equipped with a heat exchanger to remove the heat of absorbtion—i.e. heat is generated when the ethylene dissolves in the solvent and this heat exchanger removes the heat of solution. The solution absorber may be a CSTR, or alternatively, a simple plug flow tube. Thus, the heat exchanger on the solution absorber is used to provide cooled feed. In one embodiment the heat exchanger may be used to chill the feed to below ambient conditions—this is desirable to maximize reactor throughput.

In a preferred embodiment, another heat exchanger is provided that allows the feed stream to be heated. This heat exchanger may be located in direct contact with the solution absorber or—alternatively, this heat exchanger may be located between the solution absorber and the oligomerization reactor. In general, this heat exchanger will be used during non-steady state conditions (such as are encountered at start up or during a reactor upset) to quickly provide heat to the reactor.

In a highly preferred embodiment, the ethylene/solvent is fed to the CSTR through a plurality of feed ports. In one such embodiment, the feed is provided by way of a tubular ring that contains a plurality of holes and follows a circle around an interior diameter of the CSTR. The ethylene/solvent is preferably directed into liquid contained in the reactor (as opposed to gas) and even more preferably, the CSTR is operated in a liquid full mode. As used herein, the term "liquid full" means that the reactor is at least 90% full of liquid (by volume). More preferably, the ethylene is co-fed with hydrogen (i.e. hydrogen is added to the solvent/ethylene mixture). Even more preferably, the CSTR is equipped with at least two impellers that are separated from each other along the length of the agitator shaft and the ethylene/solvent/hydrogen feed is directed to the tip of one impeller and the catalyst feed is directed to the tip of the second impeller that is located at a different point along the length of the agitator shaft.

Conventional baffles that run vertically along the interior wall of the CSTR may be included to enhance mixing.

The average feed velocity for the ethylene/solvent is preferably from 0.1 to 100 mm/s. Feed velocity is calculated by dividing the volumetric flow rate ($mm^3/s$) by the total area of openings in the feed ports ($mm^2$). High feed velocity (and a plurality of feed ports) helps to rapidly disperse the ethylene. Optimum feed velocity will, in general, be influenced by a number of variables—including reactor geometry, reactor agitation and production rates. The optimization of feed rates may require that the size and number of feed ports is changed—but such optimization and changes are well within the scope of those of ordinary skill in the art.

The CSTR is preferably operated in continuous flow mode—i.e. feed is continuously provided to the CSTR and product is continuously withdrawn.

The CSTR described above may be used to provide the high degree of temperature control that we have observed to be associated with a low degree of polymer formation.

In another embodiment, the CSTR is equipped with one or more of the mixing elements described in U.S. Pat. No. 6,319,996 (Burke et al.). In particular, Burke et al. disclose the use of a tube which has a diameter that is approximately equal to the diameter of the agitator of the CSTR. This tube extends along the length of the agitator shaft, thereby forming a mixing element that is often referred to as a "draft tube" by those skilled in the art. The reactor used in this invention may also employ the mixing helix disclosed by Burke et al. (which helix is located within the draft tube and forms a type of auger or Archimedes screw within the draft tube). The use of stationary, internal elements (to divide the CSTR into one or more zones) may also be employed. In one such example, two impellers are vertically displaced along the length of the agitation shaft i.e. one in the top part of the reactor and another in the bottom. An internal "ring" or "doughnut" is used to divide the CSTR into a top reaction zone and a bottom reaction zone. The ring is attached to the diameter of the CSTR and extends inwardly towards the agitation shaft to provide a barrier between the top and bottom reaction zones. A hole in the center of the ring allows the agitation shaft to rotate freely and provides a pathway for fluid flow between the two reactions zones. The use of such rings or doughnuts to divide a CSTR into different zones is well known to those skilled in the art of reactor design.

In another embodiment, two or more separate agitators with separate shafts and separate drives may be employed. For example, a small impeller might be operated at high velocity/high shear rate to disperse the catalyst and/or ethylene as it enters the reactor and a separate (larger) impeller with a draft tube could be used to provide circulation within the reactor.

An alternative reactor design is a tubular/plug flow reactor with an external heat exchanger. Tubular/plug flow reactors are well known to those skilled in the art. In general, such reactors comprise one or more tubes with a length/diameter ratio of from 10/1 to 1000/1. Such reactors are not equipped with active/powered agitators but may include a static mixer. Examples of static mixers include those manufactured and sold by Koch-Glitsch Inc. and Sulzer-Chemtech.

Tubular reactors for use in the present invention are preferably characterized by two features:
 1) external cooling; and
 2) the use of at least one incremental ethylene feed port along the length of the tubular reactor (i.e. in addition to the initial ethylene feed at the start of the tubular reactor).

In one embodiment, the tubular reactor is a so called "heat-exchange reactor" which is generally configured as a tube and shell heat exchanger. The oligomerization reaction occurs inside the tube(s) of this reactor. The shell side provides a heat exchange fluid (for the purposes described above, namely to heat the reaction during start up and/or to cool the reaction during steady state operations).

In one embodiment, the tubes are bent so as to form a type of static mixer for the fluid passing through the shell side. This type of heat exchanger is known to those skilled in the art and is available (for example) from Sulzer-Chemtech under the trade name SMR.

It is especially preferred that the Reynolds number of the reaction fluid that flows through the tube (or tubes) of the tubular reactor is from 2000 to 10,000,000. Reynolds number is a dimensionless number that is readily calculated using the following formula:

$$Re = \frac{\rho V L}{\mu}$$

where:
V is the mean fluid velocity (SI units: m/s);
L is a characteristic linear dimension (e.g. internal diameter of tube);
$\mu$ is the dynamic viscosity of the fluid (Pa·s or N·s/m$^2$ or kg/(m·s)); and
$\rho$ is the density of the fluid (kg/m$^3$).

In one such embodiment a plurality of heat exchange reactors are connected in series. Thus, the process flow that exits the first reactor enters the second reactor. Additional ethylene is added to the process flow from the first reactor but additional catalyst is preferably not added.

In another embodiment, a CSTR is connected in series to a tubular reactor. One sub embodiment of this dual reactor system comprises a CSTR operated in adiabatic mode, followed by a tubular reactor having an external heat exchanger—in this embodiment the amount of ethylene that is consumed (i.e. converted to oligomer) in the CSTR is less than 50 weight % of the total ethylene that is consumed in the reactors. In another sub embodiment of this dual reactor system, a CSTR that is equipped with an external heat exchanger is connected to a downstream tubular reactor that is operated in adiabatic mode. In this embodiment, the amount of ethylene that is converted/consumed in the CSTR is in excess of 80 weight % of the ethylene that is consumed in the reactor. The tubular reactor may also have several different ports which allow the addition of catalyst killer/deactivator along the length of the reactor. In this manner, some flexibility is provided to allow the reaction to be terminated before the product exits from the reactor.

Another reactor design for use in the present invention is a loop reactor. Loop reactors are well known and are widely described in the literature. One such design is disclosed in U.S. Pat. No. 4,121,029 (Irvin et al.). The loop reactor disclosed by Irvin et al. contains a "wash column" that is connected to the upper leg of the loop reactor and is used for the collection of polymer. A similar "wash column" is contemplated for use in the present invention to collect by-product polymer (and/or supported catalyst). A hydrocyclone at the top end of the wash column may be used to facilitate polymer separation.

A fifth reactor design for use in the present invention is another type of heat exchange reactor in which the process side (i.e. where the oligomerization occurs) is the "shell side" of the exchanger. One embodiment of this reactor design is a so called "draft tube" reactor of the type reported to be suitable for the polymerization of butyl rubber. This type of reactor is characterized by having an impeller located near the bottom of the reactor, with little or no agitator shaft extending into the reactor. The impeller is encircled with a type of "draft tube" that extends upwards through the center of the reactor. The draft tube is open at the bottom (to allow the reactor contents to be drained into the tube, for upward flow) and at the top—where the reactor contents are discharged from the tube. A heat exchanger tube bundle is contained within the reactor and is arranged such that the tubes run parallel to the draft tube and are generally arranged in a concentric pattern around the draft tube. Coolant flows through the tubes to remove the heat of the reaction.

Monomer and solvent are preferably added by one or more feed ports that are located on the perimeter of the reactor (especially near the bottom of the reactor) and oligomerization product is withdrawn through at least one product exit port (preferably located near the top of the reactor). Catalyst is preferably added through a separate feed line that is not located close to any of the monomer feed ports(s) or product exit port(s). Draft tube reactors are well known and are described in more detail in U.S. Pat. No. 4,007,016 (Weber) and U.S. Pat. No. 2,474,592 (Palmer) and the references therein. FIG. 2 of U.S. Pat. No. 2,474,592 illustrates the use of a fluid flushing system to flush the agitator shaft in the vicinity of the agitator shaft seal. More specifically, a fluid chamber through the agitator shaft seal is connected to a source of flushing fluid (located outside of the reactor) and the channel terminates in the area where the agitator shaft enters the reactor. "Flushing fluid" is pumped through the channel to flush the base of the agitator and thereby reduce the amount of polymer build up at this location.

Another form of this type of reactor (i.e. in which the process is undertaken on the "shell" side of an internally heat exchanged reactor) is sold by ABB Lummus under the trademark Helixchanger®

Another known technique to reduce the level of fouling in a chemical reactor is to coat the reactor walls and/or internals and/or agitators with a low fouling material such as glass or polytetraflouroethylene (PTFE). The use of coatings can be especially beneficial on high fouling areas such as agitator shafts and impellers.

Reactor Control

The control systems required for the operation of CSTR's and tubular reactors are well known to those skilled in the art and do not represent a novel feature of the present invention. In general, temperature, pressure and flow rate readings will provide the basis for most conventional control operations. The increase in process temperature (together with reactor flow rates and the known enthalpy of reaction) may be used to monitor ethylene conversion rates. The amount of catalyst may be increased to increase the ethylene conversion (or decreased to decrease ethylene conversion) within desired ranges. Thus, basic process control may be derived from simple measurements of temperature, pressure and flow rates using conventional thermocouples, pressure meters and flow meters. Advanced process control (for example, for the purpose of monitoring product selectivity or for the purpose of monitoring process fouling factors) may be undertaken by monitoring additional process parameters with more advanced instrumentation. Known/existing instrumentation that may be employed include in-line/on-line instruments such as NIR infrared, Fourier Transform Infrared (FTIR), Raman, mid-infrared, ultra violet (UV) spectrometry, gas chromatography (GC) analyzer, refractive index, on-line densitometer or viscometer. The use of NIR or GC to measure the composition of the oligomerization reactor and final product composition is especially preferred.

The measurement may be used to monitor and control the reaction to achieve the targeted stream properties including but not limited to concentration, viscosity, temperature, pressure, flows, flow ratios, density, chemical composition, phase and phase transition, degree of reaction, polymer content, selectivity.

The control method may include the use of the measurement to calculate a new control set point. The control of the process will include the use of any process control algorithms, which include, but are not limited to the use of PID, neural networks, feedback loop control, forward loop control and adaptive control.

Catalyst Deactivation, Catalyst Removal and Polymer Removal

In general, the oligomerization catalyst is preferably deactivated immediately downstream of the reactor as the product exits the reaction vessel. This is to prevent polymer formation and potential build up downstream of the reactor and to prevent isomerisation of the 1-olefin product to the undesired internal olefins. It is generally preferred to flash and recover unreacted ethylene before deactivation. However, the option of deactivating the reactor contents prior to flashing and recovering ethylene is also acceptable. The flashing of ethylene is endothermic and may be used as a cooling source. In one embodiment, the cooling provided by ethylene flashing is used to chill a feedstream to the reactor.

In general, many polar compounds (such as water, alcohols and carboxylic acids) will deactivate the catalyst. The use of alcohols and/or carboxylic acids is preferred—and combinations of both are contemplated. It is generally found that the quantity employed to deactivate the catalyst is sufficient to provide deactivator to metal (from activator) mole ratio between about 0.1 to about 4. The deactivator may be added to the oligomerization product stream before or after the volatile unreacted reagents/diluents and product components are separated. In the event of a runaway reaction (e.g. rapid temperature rise) the deactivator can be immediately fed to the oligomerization reactor to terminate the reaction. The deactivation system may also include a basic compound (such as sodium hydroxide) to minimize isomerization of the products (as activator conditions may facilitate the isomerization of desirable alpha olefins to undesired internal olefins).

Polymer removal (and, optionally, catalyst removal) preferably follows catalyst deactivation. Two "types" of polymer may exist, namely polymer that is dissolved in the process solvent and non-dissolved polymer that is present as a solid or "slurry".

Solid/non-dissolved polymer may be separated using one or more of the following types of equipment: centrifuge; cyclone (or hydrocyclone), a decanter equipped with a skimmer or a filter. Preferred equipment include so called "self cleaning filters" sold under the name V-auto strainers, self cleaning screens such as those sold by Johnson Screens Inc. of New Brighton, Minn. and centrifuges such as those sold by Alfa Laval Inc. of Richmond, Va. (including those sold under the trade name Sharpies).

Soluble polymer may be separated from the final product by two distinct operations. Firstly, low molecular weight polymer that remains soluble in the heaviest product fraction ($C_{20+}$) may be left in that fraction. This fraction will be recovered as "bottoms" from the distillation operations (described below). This solution may be used as a fuel for a power generation system.

An alternative polymer separation comprises polymer precipitation caused by the removal of the solvent from the solution, followed by recovery of the precipitated polymer using a conventional extruder. The technology required for such separation/recovery is well known to those skilled in the art of solution polymerization and is widely disclosed in the literature.

In another embodiment, the residual catalyst is treated with an additive that causes some or all of the catalyst to precipitate. The precipitated catalyst is preferably removed from the product at the same time as by-product polymer is removed (and using the same equipment). Many of the catalyst deactivators listed above will also cause catalyst precipitation. In a preferred embodiment, a solid sorbent (such as clay, silica or alumina) is added to the deactivation operation to facilitate removal of the deactivated catalyst by filtration or centrifugation.

Reactor fouling (caused by deposition of polymer and/or catalyst residue) can, if severe enough, cause the process to be shut down for cleaning. The deposits may be removed by known means, especially the use of high pressure water jets or the use of a hot solvent flush. The use of an aromatic solvent (such as toluene or xylene) for solvent flushing is generally preferred because they are good solvents for polyethylene. The use of the heat exchanger that provides heat to the present process may also be used during cleaning operations to heat the cleaning solvent.

Distillation

In one embodiment of the present invention, the oligomerization product produced from this invention is added to a product stream from another alpha olefins manufacturing process for separation into different alpha olefins. As previously discussed, "conventional alpha olefin plants" (wherein the term includes i) those processes which produce alpha olefins by a chain growth process using an aluminum alkyl catalyst, ii) the aforementioned "SHOP" process and iii) the production of olefins from synthesis gas using the so called Lurgi process) have a series of distillation columns to separate the "crude alpha product" (i.e. a mixture of alpha olefins) into alpha olefins (such as butene-1, hexene-1 and octene-1). The mixed hexene-octene product which is preferably produced in accordance with the present invention is highly suitable for addition/mixing with a crude alpha olefin product from an existing alpha olefin plant (or a "cut" or fraction of the product from such a plant) because the mixed hexene-octene product produced in accordance with the present invention can have very low levels of internal olefins. Thus, the hexene-octene product of the present invention can be readily separated in the existing distillation columns of alpha olefin plants (without causing the large burden on the operation of these distillation columns which would otherwise exist if the present hexene-octene product stream contained large quantities of internal olefins). As used herein, the term "liquid product" is meant to refer to the oligomers produced by the process of the present invention which have from 4 to (about) 20 carbon atoms.

In another embodiment, the distillation operation for the oligomerization product is integrated with the distillation system of a solution polymerization plant (as disclosed in Canadian patent application no. 2,708,011, Krzywicki et al.).

If toluene is present in the process fluid (for example, as a solvent for a MAO activator), it is preferable to add water to the "liquid product" prior to distillation to form a water/toluene azeotrope with a boiling point between that of hexene and octene.

The liquid product from the oligomerization process of the present invention preferably consists of from 20 to 80 weight % octenes (especially from 35 to 75 weight %) octenes and from 15 to 50 weight % (especially from 20 to 40 weight %) hexenes (where all of the weight % are calculated on the basis of the liquid product by 100%.

The preferred oligomerization process of this invention is also characterized by producing very low levels of internal olefins (i.e. low levels of hexene-2, hexene-3, octene-2, octene-3 etc.), with preferred levels of less than 10 weight % (especially less than 5 weight %) of the hexenes and octenes being internal olefins.

In-Situ Polymerization

One embodiment of the present invention encompasses the use of components (i) (ii) and (iii) in conjunction with one or more types of olefin polymerization catalyst system (iv) to trimerise ethylene and subsequently incorporate a portion of the trimerisation product(s) into a higher polymer.

Component (iv) may be one or more suitable polymerization catalyst system(s), examples of which include, but are not limited to, conventional Ziegler-Natta catalysts, metallocene catalysts, monocyclopentadienyl or "constrained geometry" catalysts, phosphinimine catalysts, heat activated supported chromium oxide catalysts (e.g. "Phillips"-type catalysts), late transition metal polymerization catalysts (e.g. diimine, diphosphine and salicylaldimine nickel/palladium catalysts, iron and cobalt pyridyldiimine catalysts and the like) and other so-called "single site catalysts" (SSC's).

Ziegler-Natta catalysts, in general, consist of two main components. One component is an alkyl or hydride of a Group I to III metal, most commonly Al(Et) or Al(iBu)$_3$ or Al(Et)$_2$Cl but also encompassing Grignard reagents, n-butyllithium, or dialkylzinc compounds. The second component is a salt of a Group IV to VIII transition metal, most commonly halides of titanium or vanadium such as TiCl$_4$, TiCl$_3$, VCl$_4$, or VOCl$_3$. The catalyst components when mixed, usually in a hydrocarbon solvent, may form a homogeneous or heterogeneous product. Such catalysts may be impregnated on a support, if desired, by means known to those skilled in the art and so used in any of the major processes known for co-ordination catalysis of polyolefins such as solution, slurry, and gas-phase. In addition to the two major components described above, amounts of other compounds (typically electron donors) may be added to further modify the polymerization behaviour or activity of the catalyst.

Metallocene catalysts, in general, consist of transition metal complexes, most commonly based on Group IV metals, ligated with cyclopentadienyl (Cp)-type groups. A wide range of structures of this type of catalysts is known, including those with substituted, linked and/or heteroatom-containing Cp groups, Cp groups fused to other ring systems and the like. Additional activators, such as boranes or alumoxane, are often used and the catalysts may be supported, if desired.

Monocyclopentadienyl or "constrained geometry" catalysts, in general, consist of transition metal complexes, most commonly based on Group IV metals, ligated with one cyclopentadienyl (Cp)-type group, often linked to additional donor group. A wide range of structures of this type of catalyst is known, including those with substituted, linked and/or heteroatom-containing Cp groups, Cp groups fused to other ring systems and a range of linked and non-linked additional donor groups such as amides, amines and alkoxides. Additional activators, such as boranes or alumoxane, are often used and the catalysts may be supported, if desired.

A typical heat activated chromium oxide (Phillips) type catalyst employs a combination of a support material to which has first been added a chromium-containing material wherein at least part of the chromium is in the hexavalent state by heating in the presence of molecular oxygen. The support is generally composed of about 80 to 100 wt. % silica, the remainder, if any, being selected from the group consisting of refractory metal oxides, such as aluminium, boria, magnesia, thoria, zirconia, titania and mixtures of two or more of these refractory metal oxides. Supports can also comprise alumina, aluminium phosphate, boron phosphate and mixtures thereof with each other or with silica. The chromium compound is typically added to the support as a chromium (III) compound such as the acetate or acetylacetonate in order to avoid the toxicity of chromium (VI). The raw catalyst is then calcined in air at a temperature between 250 and 1000° C. for a period of from a few seconds to several hours. This converts at least part of the chromium to the hexavalent state. Reduction of the Cr (VI) to its active form normally occurs in the polymerization reaction, but can be done at the end of the calcination cycle with CO at about 350° C. Additional compounds, such as fluorine, aluminium and/or titanium may be added to the raw Phillips catalyst to modify it.

Late transition metal and single site catalysts cover a wide range of catalyst structures based on metals across the transition series.

Component (iv) may also comprise one or more polymerization catalysts or catalyst systems together with one or more additional oligomerization catalysts or catalyst systems. Suitable oligomerization catalysts include, but are not limited to, those that dimerise (for example, nickel phosphine dimerisation catalysts) or trimerise olefins or otherwise oligomerize olefins to, for example, a broader distribution of 1-olefins (for example, iron and cobalt pyridyldiimine oligomerization catalysts).

Component (iv) may independently be supported or unsupported. Where components (i) and (ii) and optionally (iii) are supported, (iv) may be co-supported sequentially in any order or simultaneously on the same support or may be on a separate support. For some combinations, the components (i) (iii) may be part or all of component (iv). For example, if component (iv) is a heat activated chromium oxide catalyst then this may be (i), a chromium source and if component (iv) contains an alumoxane activator then this may also be the optional activator (iii).

The components (i), (ii), (iii) and (iv) may be in essentially any molar ratio that produces a polymer product. The precise ratio required depends on the relative reactivity of the components and also on the desired properties of the product or catalyst systems.

An "in series" process could be conducted by first conducting the oligomerization reaction, then passing the oligomerization product to a polymerization reaction. In the case of an "in series" process various purification, analysis and control steps for the oligomeric product could potentially be incorporated between the trimerization and subsequent reaction stages. Recycling between reactors configured in series is also possible. An example of such a process would be the oligomerization of ethylene in a single reactor with a catalyst comprising components (i)-(iii) followed by co-polymerization of the oligomerization product with ethylene in a separate, linked reactor to give branched polyethylene. Another example would be the oligomerization of an ethylene-containing waste stream from a polyethylene process, followed by introduction of the oligomerization product back into the polyethylene process as a co-monomer for the production of branched polyethylene.

An example of an "in situ" process is the production of branched polyethylene catalyzed by components (i)-(iv), added in any order such that the active catalytic species derived from components (i)-(iii) are at some point present in a reactor with component (iv).

Both the "in series and "in situ" approaches can be adaptions of current polymerization technology for the process stages including component (iv). All major olefin existing polymerization processes, including multiple reactor processes, are considered adaptable to this approach. One adaption is the incorporation of an oligomerization catalyst bed into a recycle loop of a gas phase polymerization process, this could be as a side or recycle stream within the main fluidization recycle loop and or within the degassing recovery and recycle system.

Polymerization conditions when component (iv) is present can be, for example, solution phase, slurry phase, gas phase or bulk phase, with temperatures ranging from −100° C. to +300° C., and at pressures of atmospheric and above, particularly from 1.5 to 50 atmospheres. Reaction conditions, will typically have a significant impact upon the properties (e.g. density, melt index, yield) of the polymer being made and it is likely that the polymer requirements will dictate many of the reaction variables. Reaction temperature, particularly in processes where it is important to operate below the sintering temperature of the polymer, will typically, and preferably, be primarily selected to optimize the polymerization reaction conditions. Also, polymerization or copolymerization can be carried out in the presence of additives to control polymer or copolymer molecular weights. The use of hydrogen gas as a means of controlling the average molecular weight of the polymer or copolymer applies generally to the polymerization process of the present invention.

Slurry phase polymerization conditions or gas phase polymerization conditions are particularly useful for the production of high or low density grades of polyethylene, and polypropylene. In these processes the polymerization conditions can be batch, continuous or semi-continuous. Furthermore, one or more reactors may be used, e.g. from two to five reactors in series. Different reaction conditions, such as different temperatures or hydrogen concentrations may be employed in the different reactors.

Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to a purification system or the polymerization zone.

In the slurry phase polymerization process the polymerization diluent is compatible with the polymer(s) and catalysts, and may be an alkane such as hexane, heptane, isobutane, or a mixture of hydrocarbons or paraffins. The polymerization zone can be, for example, an autoclave or similar reaction vessel, or a continuous liquid full loop reactor, e.g. of the type well-known in the manufacture of polyethylene by the Phillips Process. When the polymerization process of the present invention is carried out under slurry conditions the polymerization is preferably carried out at a temperature above 0° C., most preferably above 15° C. Under slurry conditions the polymerization temperature is preferably maintained below the temperature at which the polymer commences to soften or sinter in the presence of the polymerization diluent. If the temperature is allowed to go above the latter temperature, fouling of the reactor can occur. Adjustment of the polymerization within these defined temperature ranges can provide a useful means of controlling the average molecular weight of the produced polymer. A further useful means of controlling the molecular weight is to conduct the polymerization in the presence of hydrogen gas which acts as chain transfer agent. Generally, the higher the concentration of hydrogen employed, the lower the average molecular weight of the produced polymer.

In bulk polymerization processes, liquid monomer such as propylene is used as the polymerization medium.

Methods for operating gas phase polymerization processes are well known in the art. Such methods generally involve agitating (e.g. by stirring, vibrating or fluidizing) a bed of catalyst, or a bed of the target polymer (i.e. polymer having the same or similar physical properties to that which it is desired to make in the polymerization process) containing a catalyst, and feeding thereto a stream of monomer (under conditions such that at least part of the monomer polymerizes in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerization zone and is free from, or substantially free from liquid. As is well known to those skilled in the art, if any liquid is allowed to enter the polymerization zone of a gas phase polymerization process the quantity of liquid in the polymerization zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerization zone containing polymerization catalyst, make-up monomer being provided to replace polymerized monomer, and continuously or intermittently withdrawing produced polymer from the polymerization zone at a rate comparable to the rate of formation of the polymer, fresh catalyst being added to the polymerization zone to replace the catalyst withdrawn from the polymerization zone with the produced polymer.

Methods for operating gas phase fluidized bed processes for making polyethylene, ethylene copolymers and polypropylene are well known in the art. The process can be operated, for example, in a vertical cylindrical reactor equipped with a perforated distribution plate to support the bed and to distribute the incoming fluidizing gas stream through the bed. The fluidizing gas circulating through the bed serves to remove the heat of polymerization from the bed and to supply monomer for polymerization in the bed. Thus the fluidizing gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidizing gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerization. Catalysts are preferably fed continuously or at regular internals to the bed. At start up of the process, the bed comprises fluidizable polymer which is preferably similar to the target polymer. Polymer is produced continuously within the bed by the polymerization of the monomer(s). Preferably means are provided to discharge polymer from the bed continuously or at regular internals to maintain the fluidized bed at the desired height. The process is generally operated at relatively low pressure, for example, at 10 to 50 atmospheres, and at temperatures for example, between 50 and 135° C. The temperature of the bed is maintained below the sintering temperature of the fluidized polymer to avoid problems of agglomeration.

In the gas phase fluidized bed process for polymerization of olefins the heat evolved by the exothermic polymerization reaction is normally removed from the polymerization zone (i.e. the fluidized bed) by means of the fluidizing gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidized bed polymerization process of the present invention it is desirable to provide additional cooling of the bed (and thereby improve the space time yield of the process) by feeding a volatile liquid to the bed under conditions such that the liquid evaporates in the bed thereby absorbing additional heat of polymerization from the bed by the "latent heat of evaporation" effect. When the hot recycle gas from the bed enters the beat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidizing gas stream emerging from the reactor and can be recycled to the bed with recycle gas, or can be separated from the recycle gas and then returned to the bed.

A number of process options can be envisaged when using the catalysts of the present invention in an integrated process to prepare higher polymers i.e. when component (iv) is present. These options include "in series" processes in which the oligomerization and subsequent polymerization are carried in separate but linked reactors and "in situ" processes in which a both reaction steps are carried out in the same reactor.

In the case of a gas phase "in situ" polymerization process, component (iv) can, for example, be introduced into the polymerization reaction zone in liquid form, for example, as a solution in a substantially inert liquid diluent. Components (i)-(iv) may be independently added to any part of the polymerization reactor simultaneously or sequentially together or separately. Under these circumstances it is preferred the liquid containing the component(s) is sprayed as fine droplets into the polymerization zone. The droplet diameter is preferably within the range 1 to 1000 microns.

Although not usually required, upon completion of polymerization or copolymerization, or when it is desired to terminate polymerization or copolymerization or at least temporarily deactivate the catalyst or catalyst component of this invention, the catalyst can be contacted with water, alcohols, acetone, or other suitable catalyst deactivators a manner known to persons of skill in the art.

A range of polyethylene polymers are considered accessible including high density polyethylene, medium density polyethylene, low density polyethylene, ultra low density polyethylene and elastomeric materials. Particularly important are the polymers having a density in the range of 0.91 to 0.93, grams per cubic centimeter (g/cc) generally referred to in the art as linear low density polyethylene. Such polymers and copolymers are used extensively in the manufacture of flexible blown or cast film.

Depending upon the use of the polymer product, minor amounts of additives are typically incorporated into the polymer formulation such as acid scavengers, antioxidants, stabilizers, and the like. Generally, these additives are incorporated at levels of about 25 to 2000 parts per million by weight (ppm), typically from about 50 to about 1000 ppm, and more typically 400 to 1000 ppm, based on the polymer. In use, polymers or copolymers made according to the invention in the form of a powder are conventionally compounded into pellets. Examples of uses for polymer compositions made according to the invention include use to form fibres, extruded films, tapes, spunbonded webs, molded or thermoformed products, and the like. The polymers may be blown or cast into films, or may be used for making a variety of molded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuranone stabilizers, and the like.

Fillers such as silica, glass fibers, talc, and the like, nucleating agents, and colourants also may be added to the polymer compositions as known by the art.

The present invention is illustrated in more detail by the following non-limiting examples.

EXAMPLES

The following abbreviations are used in the examples:
Å=Angstrom units
NMR=nuclear magnetic resonance
Et=ethyl
Bu=butyl
iPr=isopropyl
c*=comparative
rpm=revolutions per minute
GC=gas chromatography
$R_x$=reaction
Wt=weight
$C_4$'s=butenes
$C_6$'s=hexenes
$C_8$'s=octenes
PE=polyethylene
Part I: Preferred Ligand Synthesis
General This section illustrates the synthesis of a preferred but non-limiting ligand for use in the present invention.

All reactions involving air and or moisture sensitive compounds were conducted under nitrogen using standard Schlenk or cannula techniques, or in a glovebox. Reaction solvents were purified prior to use (e.g. by distillation) and stored over activated 4 Å sieves. Diethylamine, triethylamine and isopropylamine were purchased from Aldrich and dried over 4 Å molecular sieves prior to use. 1-Bromo-2-fluoro-benzene, phosphorus trichloride ($PCl_3$), hydrogen chloride gas and n-butyllithium were purchased from Aldrich and used as is. The methylalumoxane (MAO), 10 wt % Al in toluene, was purchased from Akzo and used as is. Deuterated solvents were purchased (toluene-$d_8$, THF-$d_8$) and were stored over 4 Å sieves. NMR spectra were recorded on a Bruker 300 MHz spectrometer (300.1 MHz for $^1$H, 121.5 MHz for $^{31}$P, 282.4 for $^{19}$F).

Preparation of $Et_2NPCl_2$ $Et_2NH$ (50.00 mmol, 5.17 mL) was added dropwise to a solution of $PCl_3$ (25.00 mmol, 2.18 mL) in diethyl ether (will use "ether" from here) (200 mL) at −78° C. After the addition, the cold bath was removed and the slurry was allowed to warm to room temperature over 2 hours. The slurry was filtered and the filtrate was pumped to dryness. The residue was distilled (500 microns, 55° C.) to give the product in quantitative yield.

$^1$H NMR (δ, toluene-d$_8$): 2.66 (doublet of a quartets, 4H, $J_{PH}$=13 Hz, $J_{HH}$=7 Hz), 0.75 (triplet, 6H, J=7 Hz).

Preparation of (ortho-F—$C_6H_4$)$_2$P-NEt$_2$

To solution of n-BuLi (17.00 mL of 1.6 M n-BuLi hexane solution, 27.18 mmol) in ether (100 mL) maintained at −85° C., was added dropwise a solution of 1-bromo-2-fluorobenzene (4.76 g, 27.18 mmol) in ether (40 mL) over 2 hours. After addition, the reaction flask was stirred for 1 hour at −78° C., resulting in a white slurry. $Et_2NPCl_2$ (2.36 g, 13.58 mmol) in ether (20 mL) was then added very slowly while the reaction temperature was maintained at −85° C. The reaction was allowed to warm to −10° C. overnight. Toluene (10 mL) was then added to the reaction flask and the volatiles were removed in vacuo. The residue was extracted with toluene and the solution was pumped to dryness. The crude product was distilled (300 microns, 100° C.) yielding 3.78 g (95%) of product. $^1$H NMR (δ, THF-d$_8$): 7.40-7.01 (4 equal intense multiplets, 8H), 3.11 (doublets of quartet, 4H, $J_{PH}$=13 Hz, $J_{HH}$=7 Hz), 0.97 (triplet, 6H, J=7 Hz). $^{19}$F NMR (δ, THF-d$_8$): −163.21 (doublet of multiplets, J=48 Hz). GC-MS. M$^+$=293.

Preparation of (ortho-F—$C_6H_4$)$_2$PCl

Anhydrous HCl$_{(g)}$ was introduced to the head space of an ethereal solution (100 mL) of (ortho-F—$C_6H_4$)P-NEt$_2$ (3.73 g, 12.70 mmol) to a pressure of 3 psi. A white precipitate formed immediately. The reaction was stirred for an additional 0.5 hours at which point the slurry was pumped to dryness to remove volatiles. The residue was re-slurried in ether (100 mL) and filtered. The filtrate was pumped to dryness yielding (ortho-F—$C_6H_4$)$_2$PCl as a colorless oil in quantitative yield. $^1$H NMR (δ, THF-d$_8$): 7.60 (m, 4H), 7.20 (m, 2H), 7.08 (m, 2H). $^{19}$F NMR (δ, THF-d$_8$): |106.94 (doublet of multiplets, J=67 Hz).

Preparation of (ortho-F—$C_6H_4$)$_2$PNH(i-Pr)

To a solution of (ortho-F—$C_6H_4$)$_2$PCl (1.00 g, 3.90 mmol) in ether (50 mL) and NEt$_3$ (3 mL) was added an ethereal solution of i-PrNH$_2$ (0.42 mL, 4.90 mmol) at −5° C. Immediate precipitate was observed. The slurry was stirred for 3 hours and filtered. The filtrate was pumped to dryness to give a colorless oil of (ortho-F—$C_6H_4$)PNH(i-Pr) in quantitative yield.

$^1$H NMR (δ, THF-d$_8$): 7.42 (m, 2H), 7.30 (m, 2H), 7.11 (m, 2H), 6.96 (m, 2H), 3.30 (septet, 1H, J=7 Hz), 2.86 (br s, 1H), 1.15 (d, 6H, J=7 Hz). $^{19}$F NMR (δ, THF-d$_8$): −109.85 (doublet of multiplets, J=40 Hz). GC-MS, M$^+$=279.

Preparation of (ortho-F—$C_6H_4$)$_2$PN(i-Pr)P(ortho-F—$C_6H_4$)$_2$ ("Ligand 1")

To a solution of (ortho-F—$C_6H_4$)$_2$PNH(i-Pr) (3.90 mmol) [made from i-PrNH$_2$ and (ortho-F—$C_6H_4$)$_2$PCl (1.00 g, 3.90 mmol)] in ether (100 mL) maintained at −70° C. was added dropwise a solution of n-BuLi (2.43 mL of 1.6 M n-BuLi hexane solution, 3.90 mmol)). The mixture was stirred at −70° C. for 1 hour and allowed to warm to −10° C. in a cold bath (2 hours). The solution was re-cooled to −70° C. and (ortho-F—$C_6H_4$)$_2$PCl (1.00 g, 3.90 mmol) was slowly added. The solution was stirred for 1 hour at −70° C. and allowed to slowly warm to room temperature forming a white precipitate. The slurry was pumped to dryness and the residue was extracted with toluene and filtered. The filtrate was pumped to dryness and recrystallized from heptane at −70° C. (2×) yielding 1.13 g (58%) of product. At room temperature this material was an oil which contained both the desired ligand (ortho-F—$C_6H_4$)$_2$PN(i-Pr)P(ortho-F—$C_6H_4$)$_2$ and its isomer (ortho-F—$C_6H_4$)$_2$P[=N(i-Pr)]P(ortho-F—$C_6H_4$)$_2$. A toluene solution of this mixture and 50 mg of (ortho-F—$C_6H_4$)$_2$PCl was heated at 65° C. for three hours to convert the isomer to the desired ligand. $^1$H NMR (THF-d8, δ): 7.35 (m, 8H), 7.10 (m, 4H), 6.96 (m, 4H), 3.94 (m, 1H), 1.24 (d, 6H, J=7 Hz). $^{19}$F NMR (THF-d$_8$, δ): −104.2 (br. s).

In a more preferred procedure the initial steps of the synthesis are conducted in pentane at −5° C. (instead of ether) with 10% more of the (ortho-F—$C_6H_4$)PCl (otherwise as described above). This preferred procedure allows (ortho-F—$C_6H_4$)$_2$PN(i-Pr)P(ortho-F—$C_6H_4$)$_2$ to be formed in high (essentially quantitative) yield without the final step of heating in toluene.

Catalyst Preparation

The term catalyst refers to the chromium molecule with the heteroatom ligand bonded in place. The preferred P—N—P ligand does not easily react with some Cr (III) molecules—especially when using the most preferred P—N—P ligands (which ligands contain phenyl groups bonded to the P atoms, further characterized in that at least one of the phenyl groups contains an ortho fluoro substituent).

While not wishing to be bound by theory, it is believed that the reaction between the ligand and the Cr species is facilitated by aluminum alkyl or MAO. It is also believed that the reaction is facilitated by an excess of Al over Cr. Accordingly, it is most preferred to add the Cr/ligand mixture to the MAO (and/or Al alkyl) instead of the reverse addition sequence. In this manner, the initiation of the reaction is believed to be facilitated by the very high Al/Cr ratio that exists when the first part of the Cr/ligand is added to the MAO.

In a similar vein, it is believed that the ligand/Cr ratio provides another kinetic driving force for the reaction—i.e. the reaction is believed to be facilitated by high ligand/Cr ratios. Thus, one way to drive the reaction is to use an excess of ligand. In another, (preferred) reaction, a mixture with a high ligand/Cr ratio is initially employed, followed by lower ligand/Cr ratio mixtures, followed by Cr (in the absence of ligand).

Part II: Ethylene Oligomerization

Batch Operation (Comparative)

A stirred reactor having a volume of about 600 cc was used in more than 20 (comparative) batch experiments. Chromium ("Cr", as chromium (III) acetylacetonate) plus (ortho-F—$C_6H_4$)$_2$PN(i-Pr)P(ortho-F—$C_6H_4$)$_2$ ("ligand 1", as described above) and methylaluminoxane ("MAO", purchased from Albemarle) were added to the reactor under a wide variety of conditions. In general, a Cr/ligand ratio of about 1/1 and Al/Cr ratio of from 100/1 to 500/1 were tested. Cyclohexane was used as solvent.

Ethylene was added on demand to maintain pressure but the reactor was operated in "batch" mode in the sense that product was not withdrawn and catalyst was not added during the reaction. Batch oligomerization experiments were typically operated for about 12-18 minutes.

The reactor was equipped with an external jacket. Hot water was run through the jacket to warm the reactor prior to start up. This was replaced with cool water to remove heat during the reaction.

The reaction produced hexene and octene in high yield and high selectivity over a range of conditions. Combined octene/hexene yields were typically from 400-500,000 grams of oligomer per gram of chromium per hour and represented more than 85% of the converted ethylene (i.e. less than 15 weight % of the ethylene was converted into butane plus $C_{10}^+$ products). Octene/hexene ratios were generally in excess of 2/1 but less than 3/1 and the purity of both streams was typically in excess of 95% alpha olefins (i.e. only small amounts of internal olefins were produced). These oligomerizations were not conducted in a liquid full reactor.

Continuous Operation

A continuous stirred tank reactor having a volume of 1000 cc was used for these experiments. A range of operating conditions were tested.

Reactor temperatures between about 40° C. and 80° C. and pressures of about 4 to 8 MPa were tested.

The reactor was fitted with external cooling jacket. Cool water from a municipal supply was run through the jacket. The reactor was operated over the course of many months. The temperature of the water supply was generally in the range of from about 10 to 20° C. depending upon the season. A "solution absorber" unit was installed to allow ethylene to be dissolved in solvent prior to being added to the reactor. The solution was also equipped with a cooling jacket (to remove heat of absorption) and thus cool the feed to the reactor. The reactor was operated "liquid full"—i.e. the feed port and product exit port were arranged such that the reactor was essentially full of liquid during the process.

MAO was purchased as a solution of methylaluminoxine (10 weight % Al in toluene) from Albemarle.

The reactor was operated in a continuous manner—i.e. product was removed from the reactor during the reaction and make-up feed was added. Typical flow rates and reactor concentrations were as follows:

Chromium (as $Cr(acac)_3$): 0.025 mmol/liter
Ligand/Cr mole ratio=1/1
Al/Cr mole ratio=300/1 (Albemarle MAO)
Ethylene feed rate=3 g/minute
MAO solution+cyclohexane~33 ml/minute The liquid fraction produced in these experiments was similar to that produced in the batch experiments—i.e. both of the octene and hexene streams were typically greater than 95% alpha olefins and octene/hexene ratio was typically at least 2/1.

Severe polymer formation was often encountered during initial attempts at continuous operation.

A hydrogen feed line was installed for a subsequent group of experiments. The addition of hydrogen did mitigate polymer formation and it became possible to operate the reactor over extended periods of time. It is important to note that the hydrogen was not observed to hydrogenate the feed or the products in any meaningful manner (i.e. no ethane, hexane or octane were detected).

The feed preparation unit and reactor were then reconfigured so that the hydrogen feed line to the reactor was removed and a hydrogen feed line to the feed preparation unit was installed. In this manner, hydrogen was contacted with the ethylene and solvent prior to being introduced to the reactor and the ethylene, hydrogen and solvent were added via a common feed line.

The reconfigured unit was successfully tested for several three hour tests and only very low levels of polymer formation were observed. However, some polymer formation was observed—especially when episodes of fluctuating reactor conditions (such as changes in pressure and/or temperature) were encountered.

Continuous Operation (Inventive)

In addition to the above described cooling jacket, the reactor was equipped with an external heating coil (i.e. the coil was external to the reactor). A reservoir of heated water was fitted to the heating coil.

Improved reactor continuity was achieved by having both of the cooling jacket and heating coil operational during the oligomerization reaction.

This inventive configuration of process equipment allows the "heating" coil to be used to add heat to the reactor when a drop in reactor temperature is observed. The cooling system is used during normal/steady state operation to remove heat of reaction.

The above described process allowed for improved reactor continuity. Some polymer build up was still observed on the impeller blade and on the agitator shaft—especially where the agitator shaft entered the reactor. Accordingly, in one preferred embodiment, the agitator shaft is flushed with process solvent—especially at the point where the agitator shaft enters the reactor.

What is claimed is:

1. A method for mitigating the formation of by-product polyethylene that is produced during a selective tetramerization of ethylene, said method comprising:
   a) providing a reactor system comprising at least one reactor, wherein said reactor system comprises:
      1) a first heat exchanger that is used to provide heat to said reactor system; and
      2) a second heat exchanger that is used to remove heat from said reactor system;
   b) contacting ethylene, a solvent, and hydrogen prior to being introduced into said at least one reactor; and
   c) contacting, in said at least one reactor, said ethylene, solvent, and hydrogen with:
      i) a catalyst comprising:
         1.1) a source of chromium that is soluble in said solvent; and
         1.2) a ligand defined by the formula $(R^1)(R^2)$—$P^1$-bridge-$P^2(R^3)(R^4)$,
            wherein $R^1$, $R^2$, $R^3$, and $R^4$ are independently selected from the group consisting of an unsubstituted phenyl group and a phenyl group having only a single ortho-fluoro-substituent;
            wherein said bridge is bonded to both phosphorus atoms and defined by the formula —$N(R^5)$—; and
            wherein $R^5$ is selected from the group consisting of hydrogen, an alkyl group, a substituted alkyl group, an aryl group, a substituted aryl group, an aryloxy group, a substituted aryloxy group, a halogen, an alkoxycarbonyl group, a carbonyloxy group, an alkoxy group, an aminocarbonyl group, a dialkylamino group, and a silyl group, and
      ii) an activator comprising an aluminoxane;
   d) selectively tetramerizing the ethylene at a temperature of from 10° C. to 100° C. and at a pressure of from 5 to 100 atmospheres in the at least one reactor
to produce a liquid product comprising octene and hexene, wherein:
   (i) the weight ratio of octene to hexene is greater than 2:1; and (ii) less than 5 weight % of the octene contains internal olefins,
wherein the formation of by-product polyethylene during said selective tetramerization of ethylene is reduced compared to the same selective tetramerization of ethylene in which only ethylene and solvent are contacted prior to being introduced into said at least one reactor and in which the ethylene and solvent are subsequently contacted with hydrogen in said at least one reactor.

2. The method of claim 1, wherein said at least one reactor comprises a liquid full continuously stirred tank reactor.

3. The method of claim 1, wherein said at least one reactor comprises a continuously stirred tank reactor and a tubular reactor downstream of the continuously stirred tank reactor,
wherein said contacting said ethylene, solvent, and hydrogen, with said catalyst and activator in said at least one reactor comprises contacting said ethylene, solvent, and hydrogen, with said catalyst and activator in said continuously stirred tank reactor; and
wherein said selectively tetramerizing the ethylene in said at least one reactor comprises:
(a) selectively tetramerizing the ethylene at a temperature of from 10° C. to 100° C. and at a pressure of from 5 to 100 atmospheres in the continuously stirred tank reactor to produce a first tetramerization product;
(b) passing said first tetramerization product from said continuously stirred tank reactor to said tubular reactor along with fresh feed comprising ethylene and solvent, wherein said fresh feed is colder than said first tetramerization product; and
(c) converting both said ethylene in the fresh feed and said first tetramerization product in the tubular reactor to said liquid product comprising octene and hexene.

4. The method of claim 3, further characterized in that said first tetramerization product is initially cooled in a heat exchanger prior to being fed to said tubular reactor.

5. The method of claim 1, wherein said at least one reactor comprises a first continuously stirred tank reactor having a first reactor volume and a second continuously stirred tank reactor having a second reactor volume,
wherein the second continuously stirred tank reactor is downstream of the first continuously stirred tank reactor,
wherein the second reactor volume is greater than the first reactor volume,
wherein said contacting said ethylene, solvent, and hydrogen, with said catalyst and activator in said at least one reactor comprises contacting said ethylene, solvent, and hydrogen, with said catalyst and activator in said first continuously stirred tank reactor; and
wherein said selectively tetramerizing the ethylene in said at least one reactor comprises:
a) selectively tetramerizing the ethylene at a temperature of from 10° C. to 100° C. and at a pressure of from 5 to 100 atmospheres in the first continuously stirred tank reactor to produce a first tetramerizion product;
b) passing said first tetramerization product from said first continuously stirred tank reactor to said second continuously stirred tank reactor along with fresh feed comprising ethylene and solvent; and
c) converting both said ethylene in the fresh feed and said first tetramerization product in the second continuously stirred tank reactor to said liquid product comprising octene and hexene.

6. The method of claim 2, wherein liquid full continuously stirred tank reactor is characterized by having an agitator shaft, wherein said agitator shaft comprises an agitator shaft seal that contains a fluid channel contained therein that permits fluid flushing of said agitator shaft.

7. The method of claim 1, further characterized in that a portion of said ethylene is dissolvent in said solvent in a solution absorber that is external to said reactor system, wherein said solution absorber is equipped with a third heat exchanger for removal of heat of absorption.

8. A method for mitigating the formation of by-product polyethylene that is produced during a selective tetramerization of ethylene, said method comprising:
a) providing a reactor system comprising at least one reactor, wherein said reactor system comprises:
1) a first heat exchanger that is used to provide heat to said reactor system; and
2) a second heat exchanger that is used to remove heat from said reactor system;
b) contacting ethylene, a solvent, and hydrogen prior to being introduced into said at least one reactor; and
c) contacting, in said at least one reactor, said ethylene, solvent, and hydrogen with:
i) a catalyst comprising:
1.1) a source of chromium that is soluble in said solvent; and
1.2) a ligand defined by the formula $(R^1)(R^2)$—$P^1$-bridge-$P^2(R^3)(R^4)$,
wherein $R^1$, $R^2$, $R^3$, and $R^4$ are independently selected from the group consisting of an unsubstituted phenyl group and a phenyl group having only a single ortho-fluoro-substituent, wherein at least one of $R^1$, $R^2$, $R^3$, and $R^4$ is a phenyl group having a single ortho-fluoro-substituent;
wherein said bridge is bonded to both phosphorus atoms and defined by the formula —$N(R^5)$—; and
wherein $R^5$ is selected from the group consisting of hydrogen, an alkyl group, a substituted alkyl group, an aryl group, a substituted aryl group, an aryloxy group, a substituted aryloxy group, a halogen, an alkoxycarbonyl group, a carbonyloxy group, an alkoxy group, an aminocarbonyl group, a dialkylamino group, and a silyl groups, group, and
ii) an activator comprising an aluminoxane;
d) selectively tetramerizing the ethylene at a temperature of from 10° C. to 100° C. and at a pressure of from 5 to 100 atmospheres in the at least one reactor provides to produce a liquid product comprising octene and hexene, wherein:
(i) the weight ratio of octene to hexene is greater than 2:1; and
(ii) less than 5 weight % of the octene contains internal olefins,
wherein the formation of by-product polyethylene during said selective tetramerization of ethylene is reduced compared to the same selective tetramerization of ethylene in which only ethylene and solvent are contacted prior to being introduced into said at least one reactor and in which the ethylene and solvent are subsequently contacted with hydrogen in said at least one reactor.

9. The method of claim 8, wherein said at least one reactor comprises a liquid full continuously stirred tank reactor.

10. The method of claim 8 wherein said at least one reactor comprises a continuously stirred tank reactor and a tubular reactor downstream of the continuously stirred tank reactor,
wherein said contacting said ethylene, solvent, and hydrogen, with said catalyst and activator in said at least one reactor comprises contacting said ethylene, solvent, and hydrogen, with said catalyst and activator in said continuously stirred tank reactor; and wherein said selectively tetramerizing the ethylene in said at least one reactor comprises:

(a) selectively tetramerizing the ethylene at a temperature of from 10° C. to 100° C. and at a pressure of from 5 to 100 atmospheres in the continuously stirred tank reactor to produce a first tetramerization product;

(b) passing said first tetramerization product from said continuously stirred tank reactor to said tubular reactor along with fresh feed comprising ethylene and solvent, wherein said fresh feed is colder than said first tetramerization product; and (c) converting both said ethylene in the fresh feed and said first tetramerization product in the tubular reactor to said liquid product comprising octene and hexene.

11. The method of claim 10, further characterized in that said first tetramerization product is initially cooled in a heat exchanger prior to being fed to said tubular reactor.

12. The method of claim 8, wherein said at least one reactor comprises a first continuously stirred tank reactor having a first reactor volume and a second continuously stirred tank reactor having a second reactor volume, wherein the second continuously stirred tank reactor is downstream of the first continuously stirred tank reactor, wherein the second reactor volume is greater than the first reactor volume, wherein said contacting said ethylene, solvent, and hydrogen, with said catalyst and activator in said at least one reactor comprises contacting said ethylene, solvent, and hydrogen, with said catalyst and activator in said first continuously stirred tank reactor; and wherein said selectively tetramerizing the ethylene in said at least one reactor comprises:

a) selectively tetramerizing the ethylene at a temperature of from 10° C. to 100° C. and at a pressure of from 5 to 100 atmospheres in the first continuously stirred tank reactor to produce a first tetramerizion product;

b) passing said first tetramerization product from said first continuously stirred tank reactor to said second continuously stirred tank reactor along with fresh feed comprising ethylene and solvent; and c) converting both said ethylene in the fresh feed and said first tetramerization product in the second continuously stirred tank reactor to said liquid product comprising octene and hexene.

13. The method of claim 9, wherein said liquid full continuously stirred tank reactor is characterized by having an agitator shaft, wherein said agitator shaft comprises an agitator shaft seal that contains a fluid channel contained therein that permits fluid flushing of said agitator shaft.

14. The method of claim 8, further characterized in that a portion of said ethylene is dissolvent in said solvent in a solution absorber that is external to said reactor system wherein said solution absorber is equipped with a third heat exchanger for removal of heat of absorption.

* * * * *